United States Patent [19]

Jarvik

[11] 4,166,466
[45] Sep. 4, 1979

[54] REPEATING HEMOSTATIC CLIP APPLYING INSTRUMENTS AND MULTI-CLIP CARTRIDGES THEREFOR

[76] Inventor: Robert K. Jarvik, 5974 Holladay Blvd., Salt Lake City, Utah 84121

[21] Appl. No.: 730,933

[22] Filed: Oct. 8, 1976

[51] Int. Cl.$^2$ .......................................... A61B 17/12
[52] U.S. Cl. ..................................... 128/325; 227/19
[58] Field of Search ............ 128/325, 334 R; 229/19; 74/22 A, 22 R, 520, 53; 72/416

[56] References Cited

U.S. PATENT DOCUMENTS

| | | | |
|---|---|---|---|
| 669,721 | 12/1901 | Holland . | |
| 1,136,149 | 4/1915 | McGowan . | |
| 1,625,602 | 4/1927 | Gould et al. . | |
| 1,948,865 | 2/1934 | Miller et al. | 128/332 |
| 2,174,152 | 9/1939 | Curtiss | 140/53 |
| 2,178,391 | 10/1939 | Curtiss | 140/55 |
| 2,268,755 | 1/1942 | Li | 128/326 |
| 2,277,139 | 3/1942 | Niemond | 1/49.1 |
| 2,371,082 | 3/1945 | Viestreich | 1/49 |
| 2,511,795 | 6/1950 | Cote | 1/49 |
| 2,638,847 | 5/1953 | Noiles | 227/120 |
| 2,689,995 | 9/1954 | Garcia | 1/187 |
| 2,713,533 | 7/1955 | Reimels | 206/56 |
| 2,898,915 | 8/1959 | Kammer | 128/326 |
| 2,898,916 | 8/1959 | Kammer | 128/328 |
| 2,968,041 | 1/1961 | Skold | 1/49.1 |
| 3,023,416 | 3/1962 | Ytreland | 1/187 |
| 3,023,417 | 3/1962 | Michel | 1/187 |
| 3,033,204 | 5/1962 | Wood | 128/326 |
| 3,040,747 | 6/1962 | Wood | 128/328 |
| 3,064,263 | 11/1962 | Powers | 1/187 |
| 3,082,426 | 3/1963 | Miles | 1/349 |
| 3,120,230 | 2/1964 | Skold | 128/329 |
| 3,169,526 | 2/1965 | Wood | 128/326 |
| 3,270,745 | 9/1966 | Wood | 128/325 |
| 3,289,456 | 12/1966 | Baldwin | 72/410 |
| 3,317,105 | 5/1967 | Astafjev et al. | 227/76 |
| 3,326,216 | 6/1967 | Wood | 128/325 |
| 3,363,628 | 1/1968 | Wood | 128/325 |
| 3,429,522 | 4/1969 | Wood | 72/410 |
| 3,463,156 | 8/1969 | McDermott | 128/325 |
| 3,631,707 | 1/1972 | Miller | 72/410 |
| 3,687,138 | 8/1972 | Jarvik | 128/326 |
| 3,837,555 | 9/1974 | Green | 227/19 X |
| 3,841,521 | 10/1974 | Jarvik | 221/75 |
| 3,844,289 | 10/1974 | Noiles | 128/334 |

Primary Examiner—Robert W. Michell
Assistant Examiner—Milford Juten
Attorney, Agent, or Firm—Mattern, Ware, Davis & Stoltz

[57] ABSTRACT

The instrument is generally shaped and operated in the manner of prior clip applying instruments. Shaped like a pair of dog-nosed pliers, the outer ends of the jaws are adapted to hold a clip which may be applied to a blood vessel with the instrument. The rearward portion of the jaws overlap and a rectangular channel is formed in one of them through which clips may be pushed by a pusher extending down the center line of the instrument. One of the jaws is adapted to receive a cartridge containing a stack of U-shaped clips which may be pushed one at a time to the distal end of the jaws by the pusher.

The instrument basically comprises only three pivoted members, the pusher and its operating linkage, and one or two springs.

Several forms of pusher-actuating means are disclosed, two of these include a bell crank and cam so that the pusher will be operated before the jaws can be closed. The third comprises a free bell crank and a pair of unbalanced springs to achieve the same object.

The cartridge is provided with a spring for urging the U-shaped stack of clips down to the pusher channel, and a clip follower for preventing misalignment of the clips in the cartridge.

These above and various other features operate together in a synergistic manner to apply a plurality of hemostatic clips in a surprisingly simple, light, instrument providing an almost conventional "feel".

25 Claims, 20 Drawing Figures

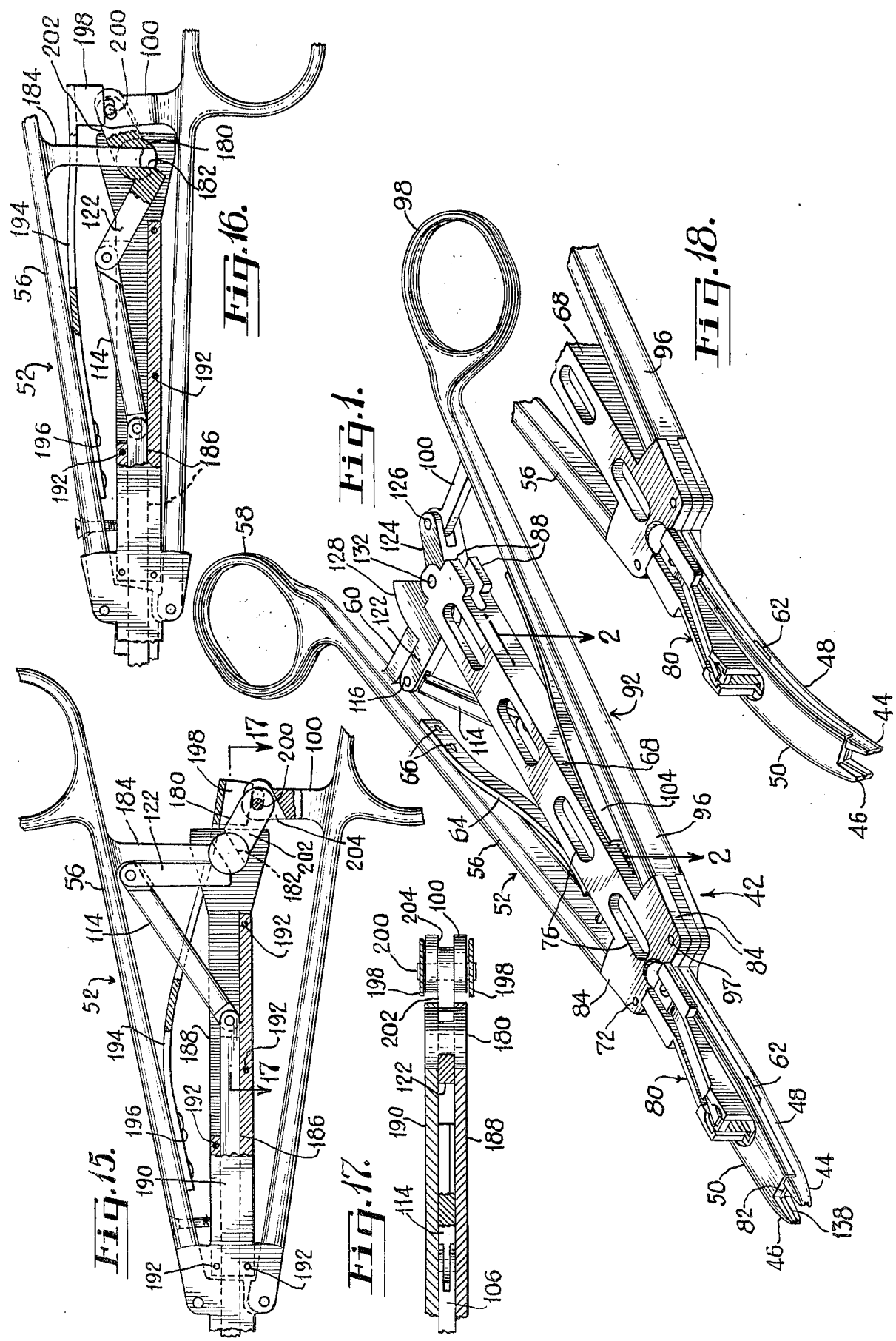

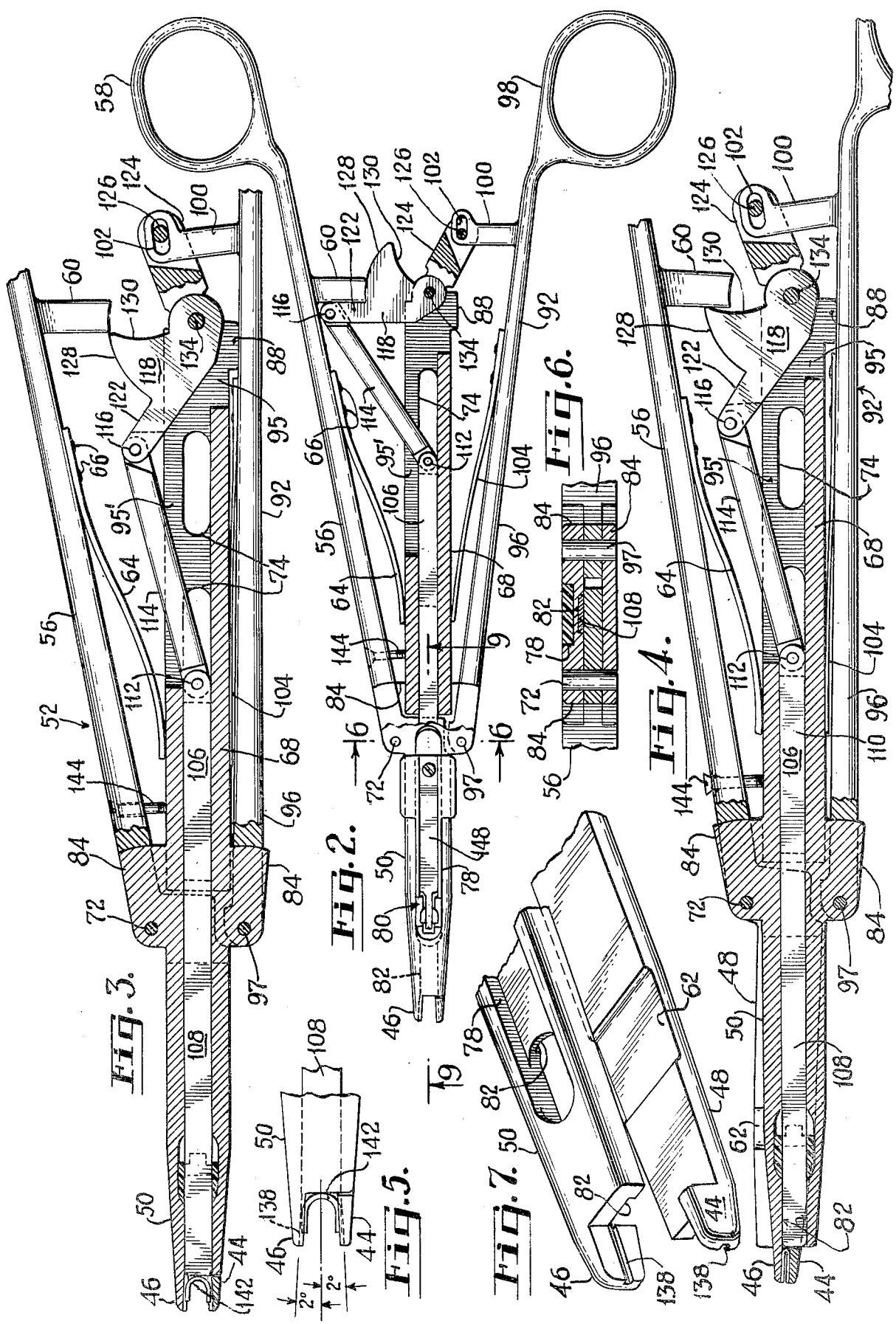

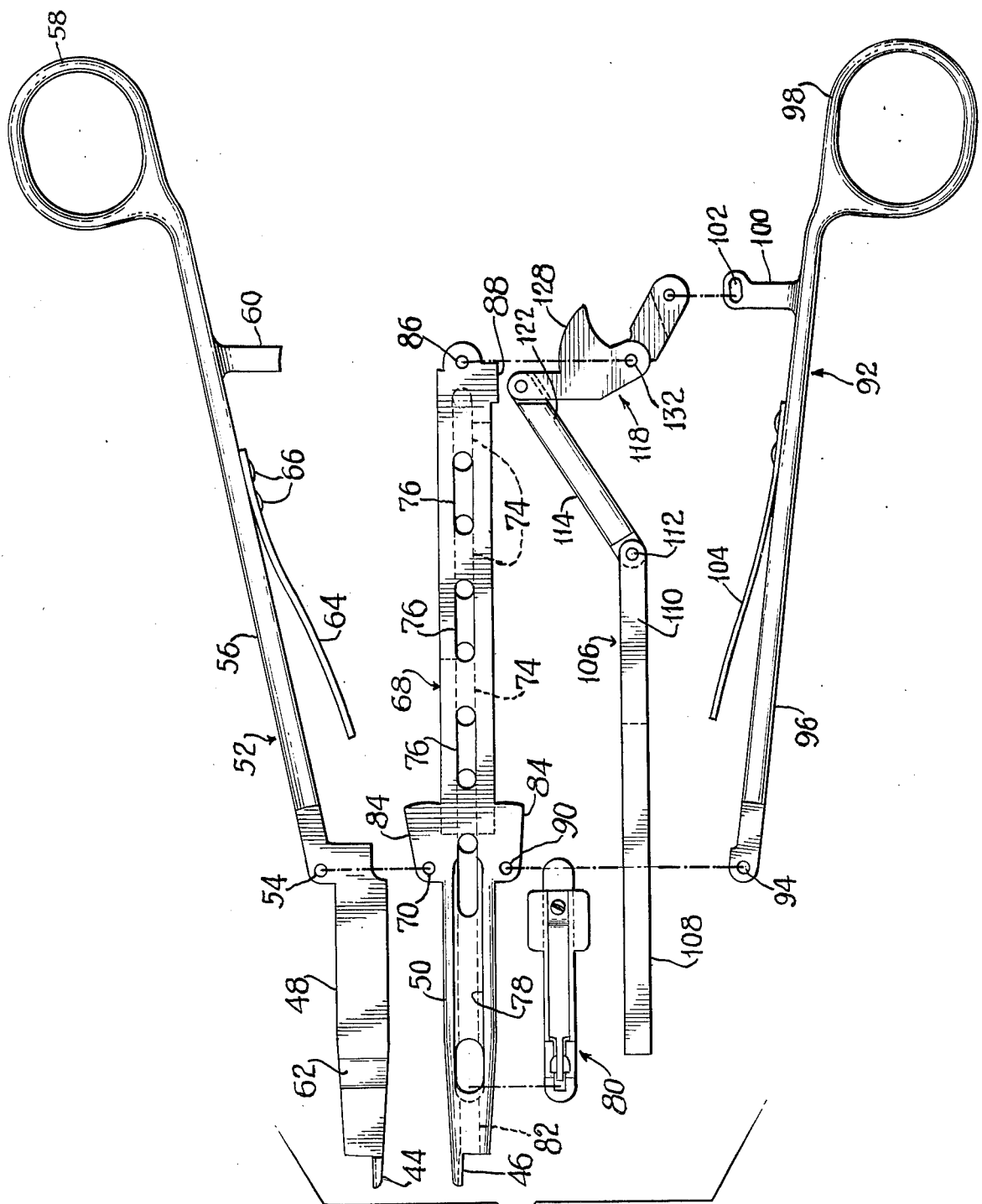

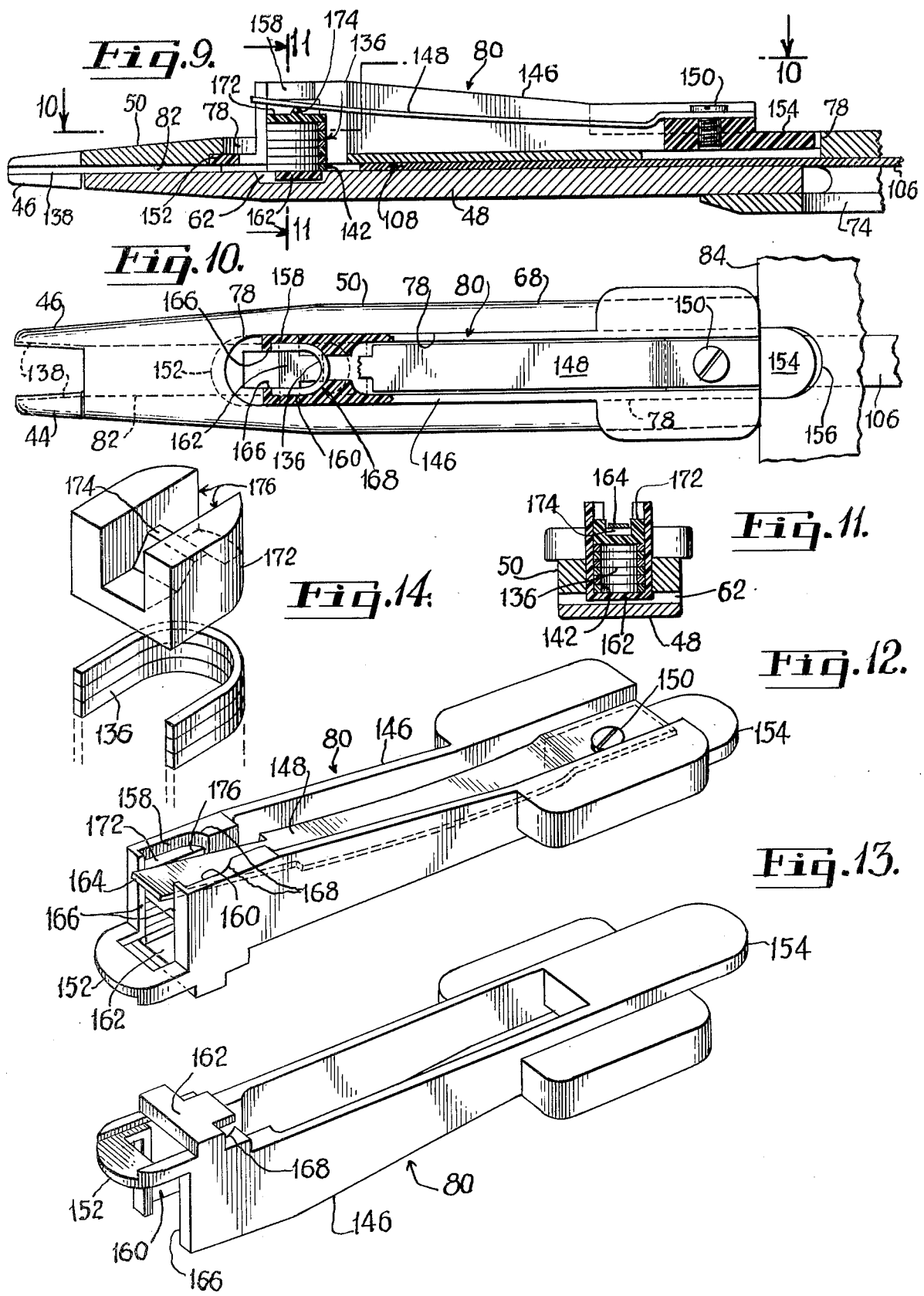

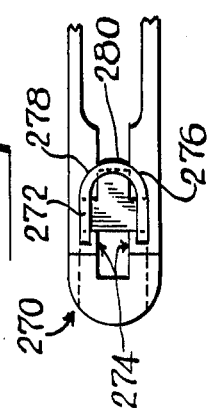
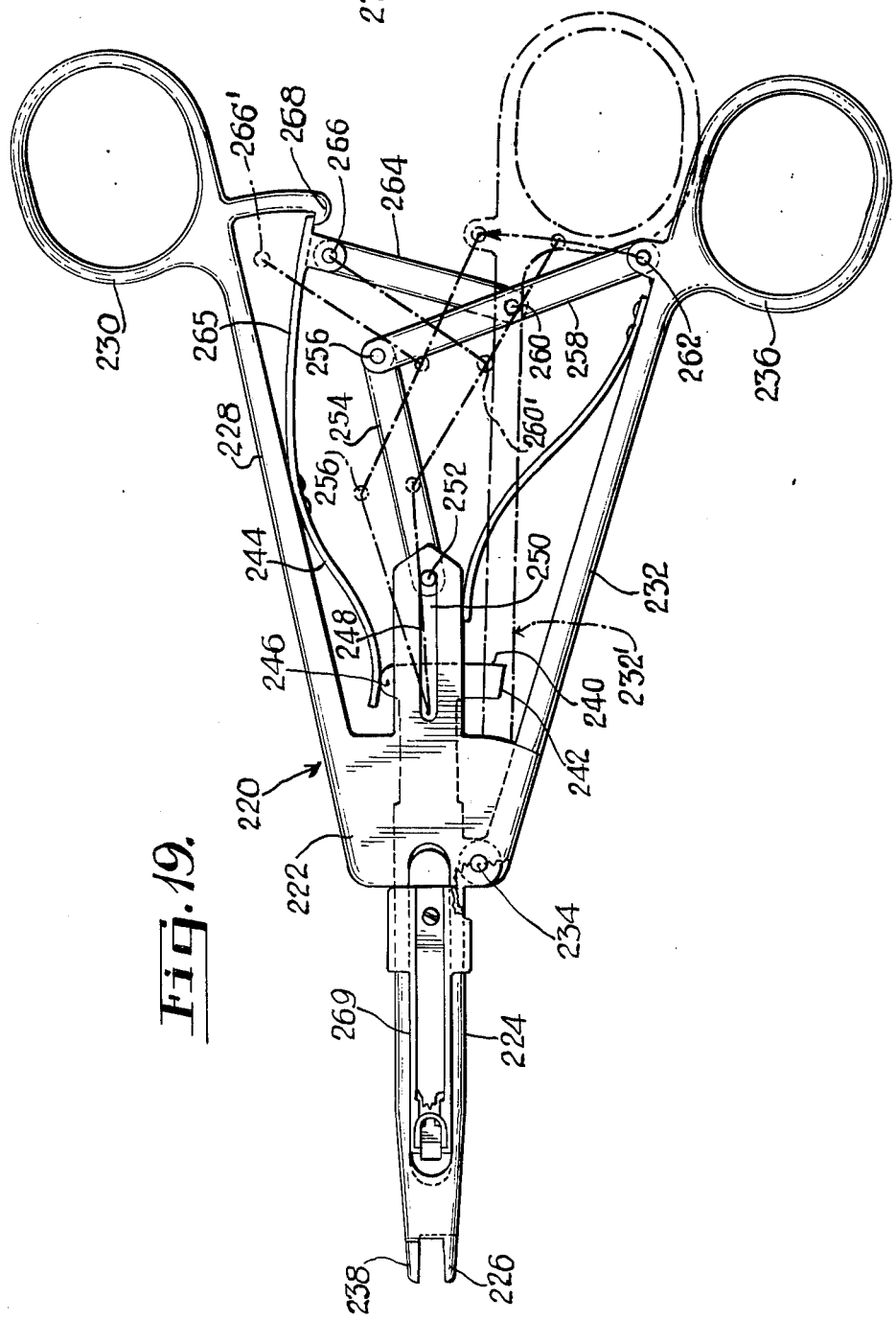

REPEATING HEMOSTATIC CLIP APPLYING INSTRUMENTS AND MULTI-CLIP CARTRIDGES THEREFOR

SUMMARY OF THE INVENTION

This invention relates to repeating hemostatic clip applying instruments and multi-clip cartridges therefor. More particularly, it relates to the rapid and repeated ligation of so called bleeders in surgical procedures.

After a surgeon has made his incision, it is necessary to clamp the tissue wherever blood is being lost due to the cutting of blood vessels. The usual technique is to clamp each so-called bleeder with a hemostat (locking dog-nosed pliers) as soon after the vessel is severed as possible. This controls the loss of blood until a ligature can be tied around the vessel. As many as 20 or more bleeders may be clamped by as many hemostats in common surgical procedures before they are tied. Thus, a single operation often requires the use of a large number of hemostats. These are handed to the surgeon and his assistants, one at a time, by the scrub nurse.

The surgical field often becomes cluttered with hemostats, which interfere with the surgeon's view and hinder the convenient application of additional hemostats. However, a good surgical practice requires the application of hemostats to all bleeders before any are tied.

The tying process requires one hand to hold the hemostat and two hands to pass the suture material around the hemostat and to form the ligature by tying a knot. This procedure thus requires two people. In addition, the ligatures must be cut and the excess suture material removed from the incision. The used hemostats must be handed to the scrub nurse and be readied for reuse. Thus, this entire technique for the achievement of hemostasis requires the coordination and teamwork of at least three people. The speed with which the bleeders may be tied off is often the determining factor in the time required for the opening stages of many surgical operations.

Many instruments have been disclosed in the prior art for ligating bleeders. However, none of these have come into general use, due to inherent deficiencies. Instruments such as disclosed in U.S. Pat. Nos. 3,033,204, 3,040,747, and 3,169,526, issued to E. C. Wood; U.S. Pat. No. 2,268,755, issued to S. F. Li; and U.S. Pat. No. 1,635,602, issued to H. G. Gould, et al, have been designed for aiding the surgeon in applying a single pretied length of suture material to a bleeder. Other instruments, such as that disclosed in U.S. Pat. No. 2,371,082 issued to F. Vistreich are designed to apply a single collar of resilient material to a deep bleeder. However, these instruments, since they apply only one ligature at a time after which another preformed ligature must be affixed to the instrument before it can then be applied to the next bleeder, do not materially reduce the amount of time or effort required in a surgical procedure. Other more complex instruments, such as disclosed in U.S. Pat. Nos. 2,898,915 and 2,898,916, issued to K. Kammer, have been devised for automatically tying a successive plurality of ligatures from a spool of suture material. I disclosed a repeating ligature gun for applying a plurality of pretied or preformed ligatures. However, these prior art instruments are complex, are difficult to load with the suture material, and, being complicated, are hard to disassemble and sterilize. None of the above prior art instruments have come into general use.

In order to obviate some of the above problems in the prior art, hemostatic clips have come into widespread use in surgery in recent years. In current surgical practice, these clips are used not only for occluding blood vessels but also for application to other structures such as nerves; for example, in vagotomy. A number of efforts have been made to facilitate loading of the clips into the instrument. This generally is done one at a time by a scrub nurse who then hands the instrument to the surgeon for application and receives the empty instrument back for reloading with another single clip. As the clips are small and difficult to handle, cartridges which hold the clips and then aid in loading the clips one at a time into the instrument have been developed. Since the clips are not firmly held in the instruments, they sometimes fall out during handling of the instrument by the scrub nurse and the surgeon prior to application.

What is needed is an instrument which will rapidly and repeatedly clamp and ligate bleeders; an instrument that can be operated with one hand; an instrument which does not leave any excess material, such as cut ends in the incision; an instrument which may be reloaded by means of a cartridge with a plurality of preformed ligatures repeatedly during an operation; and an instrument which is easy to disassemble and sterilize.

It is also desirable that the instrument handle as much as possible in the same manner as prior art surgical instruments such as towel clamps, hemostats, and clip appliers. Furthermore, it would be a highly desirable feature of such an instrument if it were adapted to apply a hemostatic clip which has already been accepted in surgical practice and in particular approved by the Food and Drug Administration (FDA) for retention in the human body as the provision of any other material or even shape of clip or preformed ligature may be occasioned with years of tests and delay before FDA approval may be secured.

OBJECTS OF THE INVENTION

It is therefore an object of the invention to improve the art of surgery.

Another object of the invention is to provide for rapid ligation of a plurality of bleeders.

Still another object of the invention is to provide preformed clips for facilitating the above objects.

A further object of the invention is to provide an instrument for applying a plurality of clips of the above character.

Another object of the invention is to provide an instrument of the above character which may be operated by one hand.

A further object of the invention is to provide an instrument of the above character which leaves no excess material or cut ends on the sutures in the body which have to be removed by the surgeon.

Still another object of the invention is to provide an instrument of the above character which is convenient to sterilize without disassembly.

Yet another object of the invention is to provide an instrument of the above character which does not require lubrication.

Still another object of the invention is to provide an instrument of the above character employing a replaceable cartridge or carrier for a plurality of preformed clips of the above character.

A further object of the invention is to provide a cartridge of the above character which is disposable.

A still further object of the invention is to provide an instrument of the above character which can affix clips to bleeders with varying tension according to the size of the vessel and type of tissue in which it occurs.

Another object of the present invention is to provide an automatic repeating clip applying instrument which will obviate the need for reloading prior to each clip application, hold the clips securely during handling so they cannot fall out, and speed surgical procedures.

It is a further object of the invention to provide a repeating instrument which has substantially the same form as present single clip applying instruments and which operates essentially the same as single clip instruments do during clip application; that is, which crushes a clip flat between two jaws when two ring handles are squeezed together thus providing the same "feel" as hemostats and clip appliers of the prior art.

To facilitate reloading of the repeating instrument, it is also an object of the present invention to provide a disposable cartridge containing a plurality of clips, which may be simply and quickly affixed to and removed from the instrument.

Still a further object is to provide an instrument with an elongated tip having delicate jaws to permit unobstructed visibility of the clip applying jaws as the clip is applied to tissue even in deep and restricted areas. To accomplish this, it is an object of the invention to provide a small and streamlined cartridge which is located remote from the tip.

Another object of the invention is to provide an instrument of the above character which is adapted to apply hemostatic ligating clips which have already been accepted in surgical practice and by the Food and Drug Administration.

A further object of the invention is to provide an instrument of the above character which is highly reliable and formed of very few moving parts.

Still another object of the invention is to provide an instrument, cartridge and clips of the above character which may be mass produced at low cost, are convenient to use, and require little or no servicing.

Other objects of the invention will in part be obvious and will in part appear hereinafter.

The invention accordingly comprises articles of manufacture possessing the features, properties and the relations of elements which will be exemplified in the articles hereinafter described, and apparatus comprising the features of construction, combinations of elements and arrangements of parts which will be exemplified in the constructions hereinafter set forth. The scope of the invention is indicated in the claims.

THE DRAWINGS

For a fuller understanding of the nature and objects of the invention, reference should be had to the following detailed description taken in connection with the accompanying drawings in which:

FIG. 1 is a top perspective view of a repeating hemostatic clip applying instrument and multi-clip cartridge therefor assembled and ready for operation.

FIG. 2 is a top view of the instrument shown in FIG. 1 in partial cross section along the plane 2—2 of FIG. 1.

FIG. 3 is an enlarged top view, partially cut away, of the instrument shown in FIG. 1 with the cross section of FIG. 2 extended and the instrument partially actuated to move a clip from the cartridge to the clip applying jaws.

FIG. 4 is an enlarged top view, partially in cross section, similar to FIG. 3 showing the instrument fully actuated to close the clip between the jaws.

FIG. 5 is an enlarged cut away view showing a detail of the jaws.

FIG. 6 is a cross-sectional view, partially cut away, taken along the line 6—6 of FIG. 2.

FIG. 7 is an enlarged exploded perspective cut away view of the clip applying jaws and a portion of the cartridge mount.

FIG. 8 is an exploded diagrammatic view showing the small number of basis parts of the instrument of FIG. 1.

FIG. 9 is an enlarged cross-sectional, cut away, view taken along the plane 9—9 of FIG. 1.

FIG. 10 is a top cross-sectional cut away view taken along the line 10—10 of FIG. 9.

FIG. 11 is a cross-sectional view taken along the line 11—11 of FIG. 9.

FIG. 12 is an enlarged top perspective view of the cartridge of the invention shown in FIG. 1.

FIG. 13 is an enlarged perspective bottom view similar to FIG. 12.

FIG. 14 is an enlarged perspective diagrammatic top view of the clips and clip follower of the cartridge of FIG. 1.

FIG. 15 is a partial cross-sectional top view, partially cut away, similar to FIG. 2, of an alternative embodiment of the invention having a different clip advancing mechanism.

FIG. 16 is a top view partially in cross-section and partially cut away similar to FIG. 15 showing the alternative embodiment with the clip advance mechanism fully advanced.

FIG. 17 is a partial cross-sectional view partially cut away taken along the line 17—17 of FIG. 15.

FIG. 18 is a top perspective view similar to FIG. 1, partially cut away, of an alternative embodiment of the invention having curved jaws for improved handling and visibility.

FIG. 19 is a top plan view of another alternative embodiment of the invention having a single pivot and a floating bell crank pusher actuating mechanism.

FIG. 20 is a top plan diagrammatic view of an alternative form of clip cartridge.

The same reference characters refer to the same elements throughout the several views of the drawings.

GENERAL DESCRIPTION

In general, the present invention is similar in function to existing single clip applying instruments such as disclosed in U.S. Pat. No. 3,713,533 in that with one actuation of the instrument, one clip is applied to tissue by being crushed thereabout by a pair of jaws. The clips are preferably also of substantially the same material size and shape when closed about the tissue as the formed clips disclosed in that patent. The instrument of this invention is so designed that in its preferred embodiment it is substantially similar in shape to present single clip applying instruments which are, in fact, designed much like numerous types of hemostats and other surgical clamps, having two ring handles and a generally elongated form which permits controlled handling and good visibility at the tip.

The present invention differs from single clip applying instruments in that a disposable cartridge is provided which holds a plurality of clips and feeds them to the instrument one at a time. Other instruments have been patented for repeatedly applying surgical clips or ligatures such as disclosed in U.S. Pat. Nos. 2,277,139, 2,968,041, 3,082,426, 3,844,289, 3,638,847, and my U.S. Pat. No. 3,841,521. However, although the need for a repeating hemostatic clip applying instrument has been recognized for decades, none is presently on the market or in clinical use.

Deficiencies in prior art repeating instruments which have led to their nonuse in clinical practice may be categorized as: overly complex instruments with a very large number of parts; instruments which obscure the physicians' field of view; gun type instruments which meet great resistance on the part of surgeons used to ring-handled plier type instruments; instruments with a great many small moving interfaces between parts which make them subject to frictional failure, extremely difficult to sterilize without disassembly, and extremely difficult to disassemble and re-assemble for good sterilization practice; lack of simple replaceable cartridges; operation which requires pulling of tissue into the instrument; and complex cartridge mechanisms which lead to prohibitive cartridge costs.

The present invention recognizes that optimal visibility to the tip, incorporation of an inexpensive multiple clip containing cartridge which can be rapidly changed, and completely automatic one hand operation, preferably with a ring handle configuration, are crucial if the instrument is to be clinically useful.

A new principle unique to all clip applying instruments is employed. A disposable cartridge, removably mounted on the instrument, holds a plurality of clips in alignment with a channel on the instrument. The instrument then removes the clips, one at a time, from the cartridge and feeds them through the channel to the jaws for application to the tissue. This principle of having the cartridge feed the clips to a position on the instrument remote from the jaws and then having the instrument feed each clip to the jaws permits the cartridge to be placed remote from the jaws, out of the line of visibility. It also permits the simplest possible construction of the jaws, that is, of only two pieces, which further aids visibility.

The instrument of this invention thus has a pair of clip applying jaws with a channel leading thereto from a remote position where a cartridge containing a plurality of clips may be removably affixed. It, in addition, has a clip feed mechanism and appropriate sequencing and spring return means so that, in operation, when a pair of ring handles are squeezed together, the forwardmost clip is removed from the cartridge, fed to the jaws and clamped about tissue positioned therebetween, and, upon release, the instrument returns to a position ready to repeat.

The instrument is basically comprised of three main portions: (1) a first pivoted member comprising a ring handle with a wide distal portion terminating in one jaw member; (2) a second pivotal member having a wide distal portion terminating in the other jaw member; and (3) an elongated ring handle. One of the distal portions is provided with a channel for a pusher to push the hemostatic clips to the jaws. This distal portion also has a cartridge receiving portion. The other distal portion acts as a cover for the channel. A linkage is provided between the ring handles and the pushing mechanism for pushing the clip out of the cartridge, forward to the jaws and then allowing the jaws to close. This is accomplished in two embodiments of the invention by providing a rotating bell crank on a proximal extension of the pusher channel member.

The bell cranks each have a cam which is engaged by an extension on one of the ring handles and is operated by an extension on the other ring handle to rotate when the handles are first closed to operate the pusher member. The cam has a cut away portion into which the extension on the opposite ring handle then falls to allow the handle to close and close the jaws.

In another embodiment of the invention, the bell crank is free floating and is connected by its center pivot to one ring handle and at one of its outer pivots to the other ring handle, and at the other outer pivot to a link connected to the pusher. This free floating bell crank linkage, by its geometry, causes the pusher to be operated against the force of the opposing spring. Thereafter the ring handle to which no jaw is connected, biassed by another spring, is able to come down against a surface of the jaw mechanism to which no ring handle is connected to close the jaws.

In general the cartridge mechanism of the invention comprises means for holding a stack of U-shaped clips aligned generally perpendicular to the plane of the pusher channel, a spring to push the clips toward the pusher channel, a bottom stop for preventing the clips from falling out of the cartridge, interlocking mechanism for interlocking the cartridge with the instrument, a clip follower between the stack of clips and the spring mechanism, and finger grips for ease of application and removal of the cartridge to or from the instrument.

SPECIFIC DESCRIPTION

More particularly, referring to FIG. 1, a repeating hemostatic clip applying instrument according to the invention is generally indicated at 42. It comprises a left and a right jaws 44 and 46 at the end of left and right distal end portions 48 and 50.

Referring to FIGS. 1 and 8, left jaw 44 is mounted to the distal end 48 of a left jaw actuating member generally indicated at 52 comprising the aforesaid distal end 48, pivot hole 54, handle shaft 56, handle ring 58, and sequencing stop extension 60. Distal end 48 is provided with a cartridge clearance cut out 62 (see also FIGS. 7 and 9). A jaws return spring 64 is attached to the handle shaft 56 by means of appropriate rivets, screws, or the like 66.

Still referring to FIGS. 1 and 8, particularly FIG. 8, the right jaw 46 and right distal extension 50 are part of a single main body generally indicated at 68. Main body 68 has a pivot hole 70, commonly pivoted to pivot hole 54 on left jaws actuating member 52 around a pivot 72 shown in FIG. 1. The main body 68 has a channel formed therein by alternating slots 74 in the bottom thereof and 76 in the top thereof which overlap to form a continuous channel which terminates at an elongated cut out 78 for receiving the cartridge generally indicated at 80.

The pusher channel is extended as clip channel 82 on the bottom side of the distal end 50 of the main body 68 to the right jaw 46.

The main body 68 is also provided with stabilizing flanges 84, bell crank pivot hole 86, a pusher actuating member stop 88, a pusher actuating member pivot 90 to which a pusher actuating member, generally indicated at 92, is pivoted by means of a pivot hole 94 therein, and a pivot 97 (FIG. 1).

Still referring to FIGS. 1 and 8, particularly FIG. 8, the pusher actuating member 92 comprises a handle shaft 96, a ring handle 98, and a bell crank actuator extension 100 having a bell crank pivot slot 102 therein. The pusher actuating member 92 is provided with a pusher return spring 104 which is preferably less strong than the jaws return spring 64.

Still referring to FIGS. 1 and 8, particularly FIG. 8, a clip pusher, generally indicated at 106, is preferably provided with a thin forward portion 108 and thick rearward portion 110. It is connected by means of pivot 112 to a pusher link 114, which in turn is connected by means of a pivot 116 to a bell crank, generally indicated at 118. As best seen in FIG. 1, bell crank 118 is provided at one end with a bifurcated arm 122, straddling a narrow portion of pusher link 114 and at its opposite end with a bifurcated arm 124, straddling bell crank actuator extension 100. Pivot pin 126 is fixed in arm 124 and rides in bell crank pivot slot 102 (FIG. 8).

Still referring to FIGS. 1 and 8, the bell crank 118 is provided with a sequencing stop surface 128 on which sequencing stop extension 60 rides, a sequencing drop-off cut out 130 and a main pivot 132 pivoted to the bell crank pivot hole 86 by means of pivot 134 (FIG. 1)—sequencing stop surface 128 and cut out 130 forming a cam.

The main body 68 is relieved at 95 for rotation of bell crank 118 and at 95' for rotation of the link 114 and rotation of bell crank 118 (FIGS. 1 and 2).

Now referring to FIGS. 9 through 13, a plurality of U-shaped hemostatic clips, generally indicated at 136, are stacked up vertically, perpendicular to the plane of the pusher 106. The clips 136 are formed of tantalum and have a uniform rectangular cross section of 0.015 wide by 0.030 high. Their arms are straight and joined by a curve of uniform radius. Their top, bottom, and outside surfaces are smooth and the inner surface is coined in a diamond knurl pattern to help retain tissue. The 2 to 1 rectangular cross section is preferred as a closed clip then has a square cross section. The clips are higher than they are wide to prevent twisting as they are closed. As shown in FIGS. 5 and 7, the jaws 44-46 are provided with clip slots 138 extending from the clip channel 82 and opening at a two degree angle therefrom. This angle assures that the jaws will be parallel when closed.

In operation, with the cartridge 80 mounted to the instrument 42, as illustrated in FIGS. 1 through 4, the pusher 106 extends to just behind the clips 136. The surgeon places the jaws 44-46 about tissues to be clipped. He then closes the two ring handles 58-98. First the pusher actuating member 92 moves about pivot 97 against pusher return spring 104, this rotates the bell crank counter-clockwise pushing the pusher 106 by means of pusher link 114 to cause the lowermost clip 142 (FIG. 9) in the clip stack 136 to be advanced through the channel 82 to between the jaws 44 and 46 as shown in FIG. 3. Since the jaws 44-46 surround tissue, the clip 142 is pushed around the tissue and remains in the jaws. Small detents (not shown) may be disposed at the forwardmost end of the clip slots 138 (FIG. 7) to stop distal motion of the clip.

During the above action, and referring to FIG. 3, the sequencing stop extension 60 has been riding on the sequencing stop surface 128 of the bell crank 118. However, once the pusher 106 has advanced to its farthest position (at this position pusher actuating member handle shaft 96 contorts stop 88), the sequencing stop extension 60 drops into the sequencing drop cut-off 130 on the bell crank 118. This allows the left jaw actuating member 52 to rotate about pivot pin 72 thereby bringing the left jaw 44 against the right jaw 46, to close the clip 142 all as shown in FIG. 4. The sequencing drop cut off 130 positively prevents return of the pusher 106 so that the clip is positively locked between tissue, jaws 44-46, and the distal end of the pusher 106 until the jaws are closed.

When the surgeon now releases the pressure on the handle shafts 56 and 96 of the left jaw actuating member 52 and pusher actuating member 92, the jaw return spring 64 first rotates left jaw actuating member 52 about pivot pin 72 under action of the jaws return spring 64 until it comes against the head of adjustment screw 144 mounted to the main body 68. Cam surface 130, being released by stop extension 60, pusher actuating member 92, under the action of pusher return spring 104, rotates about pivot 97 returning the instrument to its rest position shown in FIG. 2.

The clips may also be mounted in the cartridge 80 with their open ends slightly resiliently pressed together so that they tend to widen when released. This allows them to widen when they reach the jaws 44-46 and to be resiliently retained therein. Alternatively, the clearance between the jaws may be made smaller than the channel through which the clips are pushed, so that they are resiliently squeezed down when they reach the jaws to be retained therein. The clip slots may also be provided with transversely oriented serrations for retaining the clips therein, in the manner disclosed in U.S. Pat. No. 3,713,533.

Again, referring to FIGS. 9 through 13, the cartridge 80 comprises a main body portion 146, preferably of transparent plastic material for low cost manufacture and to allow the user to see the number of clips 136 remaining in the stack or magazine and a leaf spring 148 mounted thereto, by suitable attachment means, for example, a screw 150. Those skilled in the art will understand that spring 148 may be attached by means of a heat sealed plastic rivet or might even be integrally molded with the body 146 if a suitable plastic were employed. The cartridge 80 fits snugly into cartridge cut out 78 in right jaw extension 50. The forward end of the cartridge body 146 is provided with a forward alignment and retention tongue 152. Since the cartridge closely fits into the cut out 78, no other retention means is required. However, a detent and recess may be provided at the rear extension 154 of the cartridge body 146 and the rear end 156 of the cut out 78, or on other suitable parts of the cartridge and adjacent parts of the instrument.

The cartridge body is provided with guide surfaces 158 and 160 for guiding the clip magazine or stack 136 and at the bottom thereof with a clip platform stop 162, which fits into the cartridge clearance cut out 62 in the distal left jaw extension 48. The end of the spring 164 preferably extends through a cut out 166 to provide a visual indication of the number of clips remaining in the stack 136.

Spring pressure and friction prevents bottom clip 142 from moving either forward or rearward when the cartridge is out of the instrument. A clip follower 172 is provided for applying the force of the spring 148 against the clip stack 136 in an even manner. To this end, the clip follower 172 is provided with a clip follower fulcrum ridge 174 within a clip follower spring guide slot generally indicated at 176. Since the clip follower fulcrum ridge 174 is at the middle of the clip follower 172, the force is applied evenly to the clip stack 136 and the clip stack cannot rock out of alignment with the clip channel extension 82.

An alternative form sequencing mechanism is employed in the alternative embodiment illustrated in FIGS. 15, 16, and 17. Here, the bell crank, generally indicated at 180, is provided with a sequencing stop extension accepting slot 182 for receiving an elongated sequencing stop extension 184 mounted to the handle shaft 56 of the left jaw actuating member generally indicated at 52. The pusher slide channel 186 is formed in two pieces, 188 and 190, joined together by a plurality of fasteners 192. A single spring 194 is employed which is mounted to handle 56 by rivets or screws 196 and acts between handle 56 and bell crank actuator extension 100 by means of ears 198 acting on extended pivot pin 200.

Referring to FIG. 17 in this embodiment of the invention, the bell crank 180 is provided with a narrow arm 202 which fits into a slot 204 formed in the bell crank actuator extension 100.

In another alternative form of the invention, illustrated in FIG. 18, the thin forward portion 108 of the clip pusher 106 (not shown) is made flexible and the distal extensions 50 and 48 are curved for better visibility of the tip for use by surgeons who are used to curved or offset hemostatic instruments. The cartridge 80 may be, but need not be, conformed to this curvature which may be restricted to the portion of the instrument between the jaws 44 and 46 and the rearward end of the cartridge 80.

Now referring to FIG. 8, those skilled in the art will understand, upon reflection, that the two pivot points of pivot holes 54 and 70 and pivot holes 90 and 94 respectively, could be combined into common axis. That is, pivot hole 70 could be eliminated and pivot hole 54 moved down until it was in line with pivot holes 90 and 94 when the instrument was assembled. Furthermore, the cartridge cut out 50 and main body 68 could be formed as part of the left jaws actuating member in which case the right jaws actuating member would comprise only the right jaw 46, the distal extension 50, the pivot hole 90, and the pusher actuating member stop 88, which also acts as the right jaws actuating member when contacted by the handle shaft 96 of the pusher actuating member 92.

Now referring to FIG. 19, a single pivot instrument is generally indicated at 220. It comprises a main body 222 having a jaws extension 224 terminating in lower jaw 226. The upper finger loop extension 228 is integral with the main body 222 and terminates in upper finger loop 230. Lower finger loop extension 232 is pivoted to the main body at pivot 234 and terminates in lower finger loop 236. Upper jaw 238 is mounted to an arm also pivoted at pivot 234 and terminating at an asymmetrical T-shaped extension generally indicated at 240. The lowermost extension 242 is contacted with lower finger loop extension 232 when the two finger loops 230 and 236 are brought together and this causes the T-shape extension 240 and the upper jaw 238 to pivot about pivot 234 against the action of a spring 244 mounted at one end to finger loop extension 228 and engaging the uppermost portion 246 of the T-shaped extension 240.

The pusher mechanism is mounted in the main body 222 and a portion of the pusher channel 248 may be seen. The distal end of the pusher 250 is pivoted at pivot 252 to link 254. Link 254 is pivoted at pivot 256 to floating bell crank 258 which is pivoted at pivot 260 and connected at its other end at pivot 262 to lowermost finger loop extension 232. Pivot 260 is connected to link 264 which in turn is connected at its other end at pivot 266 to spring 265 which may be integral with spring 244 both being mounted to uppermost finger loop extension 228. Travel of spring 265 is preferably limited by stop 268 integrally formed with uppermost finger loop extension 228.

When the two finger loops 230 and 236 are brought together pivot 260 moves to position 260' and the linkages and other pivots move to the positions shown by the dotted lines and circles connected to point 260'. This causes the pusher to move fully forward pushing the clip from the cartridge 269 forward in between the jaws 226 and 238. As the front end of finger loops 230 and 236 are brought closer together, pivot 266 moves to point 266' and lowermost finger loop extension 232 moves to the postion 232' shown by dotted lines thus engaging the T-extension 240 and closing the uppermost jaw 238 against the lower jaw 226.

Now referring to FIG. 20, an alternative form of clip cartridge 270 having clipstack 272 therein may be provided with an internal clip leg or with supporting flanges 274 to prevent the clips 272 from bending inward within the cartridge 270. It will be understood that the walls of the cartridge 276 and 278 which engage the back bight 280 of the clipstack 272 need not continue all the way around the clips but merely need to engage the back of the clips to prevent them from moving backward in the stack.

Those skilled in the art will also understand that the pusher return spring 104 acting between the main body 68 and the pusher actuating member 92, could be located anywhere in the operating chain between the bell crank actuator extension, the bell crank 118, the pusher link 114 or the clip pusher 106, and the main body 68. All that is required is that a force cause the pusher member 106 to return to its normal position. This will also cause the entire mechanism including the pusher actuating member 92 to return to its normal rest position. Thus a compression spring may be located within the main body operating directly on the pusher 106 or the link pin 112 or a coil spring may operate between the main body 68 and the bell crank 118, or between the bell crank and the pusher link, or between the bell crank and the bell actuator extension. Similarly, the jaws return spring 64 may be replaced by any spring providing ultimately a rotational force between the left jaw actuating member 52 and the right jaw 46. Thus, compression springs may be mounted between the main body 68 and the handle shaft 56 or between the distal extension 48 and 50, or a coil spring may act at the pivot hole or at the pivot 72 (FIG. 1). Similarly, a coil spring acting at the pivot, between the main body 68 and the pusher actuating member 92 could replace the pusher return spring 104.

Those skilled in the art will also understand that many different sequencing mechanisms could be employed, which, upon bringing the two ring handles 58 and 98 together, would cause the pusher 106 to advance the lowermost clip 142, and then the jaws 44 and 46 to close, closing the clip. One such instrument employing a free floating bell crank is illustrated in FIG. 19. This instrument also employs a single pivot. Now referring to FIG. 19, many other sequencing mechanisms will come to mind, for example, a rack and gear mechanism for advancing the pusher. However, it will be noted by those skilled in the art that I have provided simple mechanisms employing only rotary contacts for low friction and smooth operation, which also provide very long pusher travel for relatively small closure travel between the ring handles.

I have thus provided repeating clip applying instruments and cartridges therefor, which may be employed during an operation to apply any number of hemostatic clips by merely changing pre-sterilized cartridges containing a plurality of the clips.

It will thus be seen that the objects set forth above, among those made apparent from the preceding description, are efficiently attained and since certain changes may be made in the above articles and constructions without departing from the scope of the invention, it is intended that all matter contained in the above description or shown in the accompanying drawings shall be interpreted as illustrative and not in a limiting sense.

For example, all of the clips in the cartridge need not be stacked as I have shown in FIG. 9. All that is necessary is that the bottom most clip 142 be presented at the end of the pusher and the beginning of the clip channel leading to the jaws. Thus, the clips might be mounted horizontally in a plane above the pusher, all biased by a spring forward, and another spring would be provided for biasing the forwardmost clip downward against the clip platform stop so that it would be in position at the forward end of the pusher for being pushed into the clip channel. Many other variations will readily come to mind upon reflection.

Moreover, it will be seen that I have provided a repeating hemostatic clip applying instrument involving very few parts, which is simple to operate and use, convenient to sterilize and surprisingly provides this in an instrument which handles in the manner in which surgeons have desired for many years. I have achieved this surprising result by a cunning choice of elements that synergistically work together.

It is to be understood that the following claims are intended to cover all of the generic and specific features of the invention herein described, and all statements of the scope of the invention which, as a matter of language, might be said to fall therebetween.

Having described my invention, what I claim as new and desire to secure by Letters Patent is:

1. A hemostatic clip applying instrument adapted for use with a multi-clip cartridge having a plurality of clips therein comprising:
   A. a pair of movable mating jaws towards the front of the instrument operatively connected together and adapted to be opened and closed by movement in a first plane,
      a. each of said jaws having a groove along the inner mating surface thereof in said first plane, said grooves being aligned in the same plane and mating when closed;
   B. a channel member integral with and extending from one of said jaws towards the rear of the instrument
      a. having a hemostatic clip receiving three-sided channel therein of substantially the same thickness and width as the undeformed clips, said channel aligned with and extending from said grooves towards the rear of the instrument, and substantially completely open on the fourth wide side thereof,
      b. said channel member having means for mounting a multi-clip cartridge thereto remote from said jaws; and
   C. an elongated pusher of a width and thickness at its forward end no greater than said channel for pushing said clips, one at a time, from the cartridge through said channel into said grooves in said jaws;
   D. a channel closing member integral with and extending from the other said jaws toward the rear of said instrument and mating with said open fourth side of said channel to substantially completely close the same such that said clips are closely guided on four sides as they pass through said channel.

2. The hemostatic clip applying instrument of claim 1 and:
   E. a pivot about which said pair of jaws are pivoted, and
   F. finger rings adapted to open and close said jaws, one of said finger rings formed as an integral piece with one of said jaws, and said other finger rings pivoted to said other jaws, said pair of jaws and said other finger ring being pivoted about the same pivot.

3. A hemostatic clip applying instrument as defined in claim 1 comprising a clip cartridge comprising:
   A. a plurality of U-shaped planar hemostatic clips in vertical alignment forming a U-shaped stack;
   B. stack-guide means for confining and guiding said U-shaped stack for motion along the vertical axis of said stack;
   C. spring means for biasing said stack downward;
   D. stop means at the bottom of said stack-guide means for preventing said stack from further downward motion, said stop means cooperating with said stack-guide means to form a rearward aperture for receiving said clip pusher member and a forward rectangular slot for passing a single clip;
   E. clip-guide means comprising a channel member extending horizontally from said forward slot, the width of said forward slot corresponding to the width of the channel in said clip-guide means and communicating with said channel member of the instrument; whereby said clip pusher member may push the lowermost clip of said stack through said forward slot, said clip-guide means, and said channel member to said jaws; and
   F. means for interchangeably mounting a cartridge to said channel member of the instrument.

4. A hemostatic clip applying instrument as defined in claim 1 comprising a clip cartridge comprising:
   A. a plurality of U-shaped planar hemostatic clips in vertical alignment forming a U-shaped stack:
   B. a clip follower bearing on the uppermost clip in said stack and having an outside dimension corresponding to the dimensions of said U-shaped stack;
   c. stack-guide means for confining and guiding said clip follower and U-shaped stack for motion along the vertical axis of said stack;
   D. spring means for biasing said clip follower and said stack downward;
   E. stop means at the bottom of said stack-guide means for preventing said stack from further downward motion, said stop means cooperating with said stack-guide means to form a rearward aperture for receiving said pusher and a forward rectangular slot for passing a single clip;

F. clip-guide means comprising a channel member extending horizontally from said forward slot, the width of said forward slot corresponding to the width of the channel in said clip-guide means and communicating with said channel member of the instrument; whereby said clip pusher member may push the lowermost clip of said stack through said forward slot, said clip-guide means, and said channel member to said jaws; and, G. means for interchangeably mounting a cartridge to said channel member of the instrument.

5. A clip supply cartridge removably mountable upon a clip applying instrument as defined in claim 1, said instrument adapted to permit removal of a plurality of clips from the cartridge by the instrument one at a time with each actuation of the instrument, said cartridge comprising:

A. a chamber adapted to confine a stack of generally U-shaped clips and permit motion of the stack only along its axis, having guide means parallel to the stack of clips;

B. stop means at one end of the chamber to prevent the clips from escaping from the chamber along the axis of the chamber;

C. spring means urging an entire stack of clips contained within said chamber against said stop means;

D. two openings in the chamber adjacent to the stop means permitting only the one clip in contact with the stop means to pass through by moving in a direction parallel to the arms of the U-shaped clip in a plane at substantially right angles to the axis of the clip stack, said openings providing a passageway through which said clip pusher, substantially rectangular in cross section and of the same thickness as the clips, may move;

E. means for aligning interchangeably mounting and retaining a cartridge on the instrument such that a clip in a mounted cartridge in contact with the stop means is aligned with the said channel of the instrument so that the pusher of the instrument may force said clip out of the cartridge and into said channel and as the pusher forces the clip all the way to the jaws of the instrument the remaining clips in the cartridge are blocked by the pusher from entering the position adjacent to the stop means.

6. The cartridge defined in claim 5 wherein said alignment and retention means comprises a tongue extending from the vicinity of the opening from which clips are ejected one at a time, said tongue having a slot through which the clips and the pusher may pass and being adapted to slip snugly beneath an undercut on the instrument.

7. The instrument defined in claim 1 for use with generally flat U-shaped clips of generally rectangular cross-section further defined in that said channel and forward end of said pusher are of substantially the same cross-sectional dimensions as said clips.

8. A repeating hemostatic clip applying instrument for applying undeformed open ended clips capable of passage through a channel comprising:

A. a first member
 a. formed at one end into a jaw, and
 b. formed into means remote from said jaw for receiving a cartridge containing a plurality of hemostatic clips, and
 c. having an elongated channel of substantially constant cross-section for the passage of the hemostatic clips from said cartridge receiving means to said jaw, said channel formed in said first member having substantially the same dimensions as the outer cross-section of the hemostatic clips to be applied by the instrument taken across said channel as they pass through said channel open end first;

B. a second member
 a. pivoted with respect to said first member
 b. formed at one end into a jaw;

C. a pusher for pushing clips one at a time from the cartridge through said channel to between said jaws the clip engaging end of said pusher having substantially the same cross-section as the channel;

D. a pusher actuating mechanism operatively connected to and adapted to cause said pusher to push a hemostatic clip from a cartridge down said channel to a position between said jaws and remain there against the clip as the jaws are closed, and E. a pair of handle shafts
 a. one of said handle shafts being integral with one of said members
 b. the other of said handle shafts pivoted with respect to the other of said members,
 c. and said handle shafts being operatively connected to said pusher actuating mechanism and adapted to operate the same, and then to actuate said other member, whereby when said handle shafts are closed a clip is pushed between said jaws and said jaws are closed to apply a clip while said pusher remains against the rearward end of the clip.

9. The instrument defined in claim 8 further defined in that said channel is completely open on one side thereof and:

F. said second member integrally extending from its jaw having a flat surface in sliding contact with the portion of said first member and closing said channel.

10. A repeating hemostatic clip applying instrument comprising a pair of elongated movable members terminating at a pair of hemostatic clip applying jaws, means operatively connecting said members together whereby said jaws may be opened and closed, said members having a pair of mating sliding surfaces in the mid-plane of said jaws when they are moved, one of said surfaces having a recess therein forming with said other surface a substantially closed channel having a substantially constant cross-section and of substantially the same cross-section dimensions as the outer cross-section of a clip (taken across said channel) to be applied by the instrument as they pass through said channel; means in said recessed member for receiving a stack of hemostatic clips generally aligned perpendicularly to said mating surfaces and means for biasing said clips toward said mating surfaces such that the clip nearest said mating surfaces is aligned with one end of said channel, a further recess in the mating surface of said recessed member remote from said jaws forming a channel for a movable pusher member, a pusher member which when moved therethrough forces the said nearest clip through said first channel to between said jaws, means for closing said jaws by moving said pair of members, and linkage means actuated with said closing means for causing said pusher to push a clip to said jaws before said jaws close.

11. A repeating clip applying instrument for applying generally U-shaped clips of generally rectangular outer cross-section taken across the "U" comprising:

A. first and second elongated lever arms
   a. operatively connected together for relative rotation about a common axis,
   b. each terminated at one end to form one of a pair of cooperating jaws,
   c. a first rectangular channel of constant cross-section in one of said lever arms of substantially the same cross-sectional dimensions as the said cross-section of the U-shaped clips, said channel beginning at said jaws,
   d. a second channel in said one lever arm, remote from said jaws communicated with said first channel, and oriented at an angle thereto;
B. a least two U-shaped clips stacked in said second channel in a U-shaped vertical stack;
C. means forcing said clips down said second channel towards said first channel;
D. pusher means for pushing the one of said two clips at said first channel down said first channel the forward end of said pusher of substantially the same cross-sectional dimensions as said first channel; and
F. hand operated sequencing means operatively connected to said lever arms for operating said pusher to push said clip between said jaws, and said sequencing means then closing said jaws.

12. The instrument defined in claim 11 wherein said first channel is aligned with the center line of said instrument as defined by the intersection of the plane of the instrument and a perpendicular plane passing midway between the open jaws and through the center of said channel and said axis is offset therefrom.

13. In a hemostatic clip applying instrument having a pair of jaws for applying hemostatic clips, a pair of closable handle shafts operated in a manner similar to the handle shafts of a conventional hemostat, a channel member having a channel for hemostatic clips leading to the jaws and a pusher having a jaw end and a remote end for pushing a clip down said channel; a reciprocating mechanism operated by closing the pair of handle shafts comprising:
   A. a bell crank having a pivot fixed with respect to said channel member and having a cam surface thereon comprising a surface of constant radius and a drop-off, and two lever arms, one of said lever arms pivoted to one of said handle shafts, the other of said lever arms pivoted to a connecting link pivotably connected to the remote end of said pusher; and,
   B. a cam follower mounted to the other of said handle shafts adapted to ride on said constant radius portion of said cam during the first part of the closing motion between said handle shafts and to then drop into said drop-off during the second part of the closing motion between said handle shafts.

14. In a hemostatic clip applying instrument having a pair of jaws for applying hemostatic clips, a pair of closable handle shafts operated in a manner similar to the handle shafts of a conventional hemostat, a channel member having a channel for hemostatic clips leading to the jaws and a pusher for pushing a clip down said channel toward said jaws; a reciprocating mechanism operated by closing the handle shafts for reciprocating the pusher along the center line thereof, comprising:
   A. a first link having one end pivoted to the end of said pusher remote from said jaws;
   B. a bell crank rotatable about an axis fixed with respect to said channel and having one leg pivoted to the other end of said first link;
   C. a second link having one end pivoted to the other leg of said bell crank and the other end pivoted to one of said handle shafts.

15. The hemostatic clip applying instrument of claim 1; and
   E. a pair of handles, pivoted with respect to each other and operatively connected to open and close said jaws; and
   F. automatic sequencing means operated by said handles and connected to said pusher to keep said jaws at a spacing where a clip may be held therebetween, and then actuate said pusher to push a clip from the cartridge through said channel into said grooves and between said jaws, and said sequencing means thereafter closing said jaws.

16. The hemostatic clip applying instrument of claim 15 wherein said sequencing means is adapted to cause said pusher to dwell at its furthest advance against the rear of the clip between said jaws as said jaws are closed.

17. A repeating surgical clip applying instrument having a pair of delicate clip applying jaws, means to removably mount a clip retaining and dispensing cartridge remote from the jaws, a pair of ring handles, a clip pusher; and sequencing, actuating, and spring return means such that with the jaws placed about the tissue to which a clip is to be applied, with a single, uninterrupted motion of the surgeon's hand, consisting of squeezing the ring handles together, the instrument sequentially (A) removes one clip from the cartridge, (B) feeds the clip to a position between the jaws about the tissue, (C) flattens the clip about the tissue, and (D) upon release of the ring handles, spring means return the instrument to its original position, ready to repeat; said instrument comprising:
   A. a pair of clip applying jaws, each having a mating clip slot, adapted when said jaws are open to receive a clip positioned between the jaws in said clip slots and to then crush the clip flat about tissue contained therebetween when the jaws are brought together;
   B. a pair of jaws actuating members having one of said jaws mounted at the end of each member, said members pivoted with respect to each other having stop means permitting motion only between a fully open position where said jaws are separated just enough to permit a non-deformed clip to fit therebetween, and a closed position such that the jaws contact one another,
      a. the first of said jaws actuating members having an elongated slot with two equal short sides, substantially the same height as a clip, and one long side substantially the same width as an open clip, the other side being completely open and means for mounting thereupon a clip retaining and dispensing cartridge such that one clip within said cartridge is aligned with said slot,
      b. the second of said jaws actuating members having a flat surface in sliding contact with the first jaws actuating member, which covers the open side of the slot in said first member such that an elongated channel of substantially rectangular cross-section is formed which does not substantially change in volume or dimension when the jaws are moved between the fully open and closed positions, c. the channel formed between said first and second jaws actuating members having two portions aligned with one another and a gap therebetween remote from said jaws in which a portion of a cartridge retaining a clip therein may be positioned, such that the clip is aligned with the channel, said channel further defined in that, the first portion has substantially the same width and height as an unclosed clip and has sidewalls which stabilize each arm of the clip and guide the clip as it is moved by a pusher from the cartridge to a position between the jaws when they are in the fully open position; the second portion extends from the gap generally towards the ring handles and is adapted to stabilize and align the pusher with a portion of the cartridge containing the clip, which extends into said gap;

C. an elongated clip pusher substantially the same cross-section as the channel, adapted for axial motion within the channel such that the tip of the pusher may move from said second portion of the channel across said gap and through said first portion of the channel to a position where said tip is aligned with the open end of the channel adjacent to the jaws;

D. a pair of handle shafts:
  a. a first of which is formed integral with one of the jaws' actuating members,
  b. a second of which is mounted movably about a pivot such that the two ring handles may move towards and away from one another;

E. a linkage operably interconnecting said second shaft with said pusher to move the pusher axially within the channel when the ring handles are moved with respect to one another;

F. sequencing means which maintain the jaws in the fully open position whenever the tip of the pusher is not aligned with the end of the channel adjacent to the jaws;

G. jaws' actuating means operably interconnecting the two jaws such that, when said sequencing means permit, the jaws may be forced together thereby; and H. spring means urging the shafts apart.

18. The repeating surgical clip applying instrument defined in claim 17 wherein a portion of each of the jaws' actuating members in the vicinity of the cartridge and jaws are curved, a portion of the channel is curved, and the height of said channel being slightly larger than an open clip to allow passage thereof, and the pusher is adapted flex as it follows the curvature of the channel.

19. The repeating surgical clip applying instrument defined in claim 17 wherein said means for mounting thereupon a clip retaining and dispensing cartridge comprise:

A. an elongated slot in one jaws actuating member, said slot further defined as
  a. of substantially the same width as the portion of the cartridge which mounts therein,
  b. of substantially the same length as a portion of the cartridge which mounts therein,
  c. axially aligned with the channel of the instrument
  d. laterally displaced from said channel and
  e. having an opening communicating with a gap in said channel;

B. an undercut in said jaws actuating member at the end of the elongated slot closest to the jaws, of appropriate dimensions to permit a projecting alignment tongue of the cartridge to slide snugly therein, and thus align a clip retained within the cartridge with the channel of the instrument.

20. A repeating clip applying surgical instrument adapted to flatten generally planar U-shaped clips about tissue in which all operative motions of the parts of the instrument itself occur substantially in one single plane, said instrument adapted to mount interchangeable clip retaining and dispensing cartridges each, when mounted, having a stack of clips which move at substantially right angles to the plane of motion of the instrument's parts, said instrument comprising:

A. a pair of jaws' actuating members with a slotted jaw mounted on the end of each, pivoted to permit motion of the jaws towards and away from one another within a plane,
  a. the first of said jaws' actuating members formed integral with a first handle shaft,
  b. one of said jaws's actuating members having a channel formed therein substantially the same width and height as measured across said "U" as a single, open clip,
  c. the other of said jaws' actuating members having a flat surface which completely covers said channel, thereby forming a closed channel which does not change in dimension or volume as the jaws-actuating members move relative to one another about the pivot,
  d. said channel adapted to guide a clip to the jaws from a clip-retaining and dispensing cartridge affixed to the instrument at a position remote from the jaws;

B. a second handle shaft pivotally interconnected with the first handle shaft to move within the same plane as the jaws' actuating members;

C. an elongated pusher of substantially the same width and height as a single open clip, adapted to move axially within said channel, and remove one clip at a time from the cartridge and push said clip to a position between the jaws; and D. sequencing and spring return means adapted to permit the fully automatic repeating operative cycle of the instrument in which, upon squeezing the handle shafts together, the pusher removes one clip from the cartridge and forces it to a position between the fully open jaws, which thereafter flatten the clip about tissue, and following release of the handle shafts the instrument returns to a position ready to apply a subsequent clip, said means comprising
  a. a spring urging said jaws' actuating members apart against a stop such that the jaws are open just wide enough to receive a clip ejected therebetween from the channel,
  b. a linkage incorporating a dwell mechanism operably interconnecting the handle shafts and pusher, adapted to move the pusher from its rest position to the position in which one end of said pusher is aligned with the end of the channel and thereafter dwell in said position as the handle shafts are brought together;
  c. a spring urging said handle shafts apart;
  d. an extension of the jaws' actuating member not formed integral with one handle shaft adapted to be contacted by the handle shaft not formed integral with a jaws' actuating member, during the portion of the operative cycle in which the pusher remains stationary, such that through contact with said jaws' actuating member said handle shaft forces the jaws together.

21. The instrument as defined in claim 20 having a curve in the region of the jaws such that the handle, shafts, linkage, springs, and pusher lie within a plane when no external forces are applied to the instrument and the part of the jaws actuating members and jaws are curved out of the plane.

22. A repeating clip applying surgical instrument, adapted to flatten generally U-shaped clips about tissue with a single, uninterrupted motion of the surgeon's hand, consisting of squeezing a pair of handles together, in which a pair of generally parallel-spaced jaws remain motionless during a first period of the functional cycle of the instrument while a clip is removed from a cartridge and fed therebetween through a channel by a pusher and during a second period of said cycle the pusher remains motionless, blocking the end of said channel to prevent the clip from re-entering it while the jaws are forced together, tightening the clip about the tissue, said instrument comprising:

A. a pair of clip-applying jaws supported and actuated by a pair of pivotally connected jaws actuating members, movable between a separted position, in which the jaws are just widely enough spaced to receive therebetween a non deformed clip, and a closed position in which the jaws contact one another;

B. an opening at one end of the jaws when they are in the separated position, which permits them to be positioned about tissue to which a clip is to be applied;

a channel of substantially the same width as the undeformed clips as measured across the "U", having three sides formed within a first jaws' actuating member, the fourth side consisting of a surface of the second jaws' actuating member, one end of said channel having an opening through which a generally U-shaped clip may be ejected between the separated jaws and positioned about tissue contained therebetween;

D. a pusher of substantially the same width as the clips and channel adapted to move axially within said channel and push a clip out of a removable clip-retaining and dispensing cartridge, through the channel and to a position about tissue located between the separated jaws;

E. a pair of handle shafts terminating in rings, the first of said shafts formed integral with the first of said jaws' actuating members, and the second of said handle shafts pivotally connected to the second jaws' actuating member and operably connected to the pusher by a linkage;

F. a dwell mechanism incorporated with said linkage such that squeezing the ring handles together first moves the pusher axially within the channel until the tip of the pusher closest to the jaws is aligned with and closes off the end of the channel until the tip of the pusher closest to the jaws is aligned with and closes off the end of the channel and then the dwell occurs and the pusher remains stationary while the handles are further brought together;

G. an extension of the second jaws' actuating member in line with the path of motion of the second handle shaft such that said handle shaft contacts the extension and forces the jaws closed during the dwell of the pusher;

H. spring means acting between the first and second jaws actuating members tending to separate the jaws;

I. spring means acting to force the two handle shafts apart; and

J. means to removably mount a clip retaining and dispensing cartridge to the instrument whereby one clip within the cartridge is aligned with the channel.

23. The repeating surgical clip applying instrument defined in claim 22, wherein a portion of each of the jaws' actuating members in the vicinity of the cartridge and jaws is curved, a portion of the channel formed within the jaws' actuating member is curved, the pusher is adapted flex as it follows the curvature of the channel, and said curvature is out of the plane of motion of the ring handles.

24. The repeating surgical clip applying instrument defined in claim 22, wherein said means for mounting thereupon a clip retaining and dispensing cartridge comprises:

A. an elongated slot in one jaws' actuating member, said slot further defined as
  a. substantially the same width as the portion of the cartridge which mounts therein
  b. substantially the same length as a portion of the cartridge which mounts therein
  c. axially aligned with the channel of the instrument
  d. laterally displaced from said channel
  e. having an opening communicating with a gap in said channel; and B. an undercut in said jaws' actuating member at the end of the elongated slot closest to the jaws, of appropriate dimensions to permit a projecting alignment tongue of the cartridge to slide snugly therein, and thus align a clip retained within the cartridge with the channel of the instrument.

25. The repeating surgical clip applying instrument defined in claim 22 wherein the channel is formed by a three-sided slot in one of the jaws' actuating members upon which the cartridge mounts, and the channel is covered by a flat surface of the other jaws' actuating member such that the channel does not change substantially in cross-sectional shape or volume when the two jaws' actuating members move with respect to one another.

* * * * *